United States Patent
Umezaki et al.

(10) Patent No.: US 9,642,807 B2
(45) Date of Patent: May 9, 2017

(54) METHOD FOR PRODUCING STARCH GRANULES, AND ORALLY DISINITEGRATING TABLET

(71) Applicant: JAPAN CORN STARCH CO., LTD, Minato-ku (JP)

(72) Inventors: Masao Umezaki, Hekinan (JP); Hiroshige Murase, Hekinan (JP); Toshio Uno, Tokyo (JP); Toshiyuki Niwa, Nagoya (JP)

(73) Assignee: JAPAN CORN STARCH CO., LTD, Minato-ku (JP)

( * ) Notice: Subject to any disclaimer, the term of this patent is extended or adjusted under 35 U.S.C. 154(b) by 88 days.

(21) Appl. No.: 14/397,042

(22) PCT Filed: Apr. 23, 2013

(86) PCT No.: PCT/JP2013/061900
§ 371 (c)(1),
(2) Date: Oct. 24, 2014

(87) PCT Pub. No.: WO2013/161805
PCT Pub. Date: Oct. 31, 2013

(65) Prior Publication Data
US 2015/0141525 A1 May 21, 2015

(30) Foreign Application Priority Data
Apr. 27, 2012 (JP) ................................. 2012-103267

(51) Int. Cl.
| | | |
|---|---|---|
| *A61K 9/20* | (2006.01) | |
| *C08J 3/12* | (2006.01) | |
| *C08B 30/14* | (2006.01) | |
| *A61K 9/00* | (2006.01) | |
| *A61K 9/16* | (2006.01) | |
| *C08L 3/02* | (2006.01) | |
| *A61K 47/36* | (2006.01) | |
| *C08B 30/06* | (2006.01) | |
| *C08B 30/12* | (2006.01) | |

(52) U.S. Cl.
CPC .......... *A61K 9/2059* (2013.01); *A61K 9/0056* (2013.01); *A61K 9/1652* (2013.01); *A61K 9/2054* (2013.01); *A61K 9/2095* (2013.01); *A61K 47/36* (2013.01); *C08B 30/06* (2013.01); *C08B 30/12* (2013.01); *C08B 30/14* (2013.01); *C08J 3/12* (2013.01); *C08L 3/02* (2013.01); *C08J 2303/02* (2013.01)

(58) Field of Classification Search
None
See application file for complete search history.

(56) References Cited

U.S. PATENT DOCUMENTS

| | | |
|---|---|---|
| 5,164,014 A | 11/1992 | Brancq et al. |
| 5,718,770 A | 2/1998 | Shah et al. |
| 5,720,822 A | 2/1998 | Jeffcoat et al. |
| 5,725,676 A | 3/1998 | Chiu et al. |
| 5,932,017 A | 8/1999 | Chiu et al. |
| 6,010,574 A | 1/2000 | Jeffcoat et al. |
| 6,221,420 B1 | 4/2001 | Thomas et al. |
| 6,231,675 B1 | 5/2001 | Chiu et al. |
| 6,261,376 B1 | 7/2001 | Jeffcoat et al. |
| 2001/0017133 A1 | 8/2001 | Chiu et al. |
| 2008/0085309 A1* | 4/2008 | Tsushima ............. A61K 9/0056 424/464 |
| 2009/0163604 A1* | 6/2009 | Kakizawa ............ A61K 9/2018 514/781 |
| 2010/0159101 A1 | 6/2010 | Berckmans et al. |
| 2010/0330369 A1 | 12/2010 | Veelaert |
| 2011/0021643 A1 | 1/2011 | Endo et al. |
| 2011/0288146 A1* | 11/2011 | Deorkar ................ A61K 9/2027 514/423 |

(Continued)

FOREIGN PATENT DOCUMENTS

| | | |
|---|---|---|
| EP | 2 261 263 A1 | 12/2010 |
| JP | 49-110819 | 10/1974 |
| JP | 53-099340 | 8/1978 |
| JP | 53-99340 | 8/1978 |
| JP | 58-27774 | 6/1983 |
| WO | WO 96/00506 A1 | 1/1996 |
| WO | WO 96/04315 A1 | 2/1996 |

(Continued)

OTHER PUBLICATIONS

Extended European Search Report issued Aug. 11, 2015 in Patent Application No. 13781762.3.
Office Action issued May 7, 2015 in Japanese Patent Application No. 2014-512605 (with English language translation).
Fumikazu Tamamushi, et al., "Starch Paste" Iwanami Dictionary of Physics and Chemistry, $3^{rd}$ edition, 1971, p. 920 (with partial English translation).
International Search Report issued Jul. 2, 2013, in PCT/JP13/061900 filed Apr. 23, 2013.

*Primary Examiner* — Susan Tran
*Assistant Examiner* — William Craigo
(74) *Attorney, Agent, or Firm* — Oblon, McClelland, Maier & Neustadt, L.L.P.

(57) ABSTRACT

A method for producing starch granules suitable as an excipient for an orally disintegrating tablet. Fluidized bed granulation is performed by spraying a starch paste in small amounts while a β-starch is being fluidized using an air-fluidized bed. Subsequently, fluidized bed drying is performed at a temperature equal to or higher than the gelatinization temperature of the β-starch. This yields starch granules having a high degree of gelatinization in comparison with the amount of α-starch adhered to the β-starch by the spraying of the starch paste. These starch granules alone impart satisfactory oral disintegratability and breaking strength to the tablet. Accordingly, when used as an excipient during tableting of orally disintegrating tablets, other auxiliary excipients such as saccharides or crystalline cellulose need not be added.

13 Claims, 6 Drawing Sheets

(56) References Cited

U.S. PATENT DOCUMENTS

2013/0029026 A1    1/2013  Berckmans et al.

FOREIGN PATENT DOCUMENTS

| WO | WO 2008/032767 A1 | 3/2008 |
| WO | WO 2009/013346 A1 | 1/2009 |
| WO | WO 2009/103514 A1 | 8/2009 |
| WO | WO 2011/124656 A1 | 10/2011 |

* cited by examiner

METHOD FOR PRODUCING STARCH GRANULES, AND ORALLY DISINTEGRATING TABLET

TECHNICAL FIELD

The present invention relates to a method for producing starch granules which are used as an excipient for an orally disintegrating tablet, and an orally disintegrating tablet in which the starch granules are used as an excipient.

In the following description, the units "parts" indicating blend amounts and the units "%" indicating concentration are both mass-based units, unless specifically stated otherwise.

Further, in the present description and the claims, the meanings of various terms are described below.

"Starch" . . . has the meaning of the substance name, but also means an aggregate of starch particles.

"β-Starch" . . . a crystalline state starch which yields interference rings with natural X-rays (see "Dictionary of Chemistry 1" (Kagaku Daijiten 1), edited by the Dictionary of Chemistry Editorial Committee (1962 Jul. 31), published by Kyoritsu Shuppan Co., Ltd., page 428).

"Starch paste" . . . an aqueous dispersion of starch obtained by subjecting β-starch in an aqueous dispersion medium to a heat dispersion treatment at a temperature equal to or higher than the gelatinization temperature until a uniform phase is formed.

"α-Starch (gelatinized starch, α-type starch)" . . . an amorphous state starch which displays no interference rings with X-rays, obtained by performing a heat treatment at a temperature equal to or higher than the gelatinization temperature, or a treatment with a swelling reagent, in the presence of water (moisture) (reference source: same as above).

BACKGROUND ART

In recent years, not only in the field of pharmaceuticals, but also in fields such as health foods and nutritional foods, the development and marketing of products in the form of tablets has become increasingly common. Against this background, orally disintegrating tablets which can be taken without water are attracting much attention. Orally disintegrating tablets must have oral disintegratability that allows rapid disintegration inside the mouth, but must also have sufficient tablet strength (hereafter referred to as "hardness") that no problems arise from the production steps through to the packaging steps, shipping, and subsequently handling. This oral disintegratability and this hardness are usually mutually opposing properties, and therefore the tableting of orally disintegrating tablets has typically required the addition of various additives and the use of special production devices. Further, the tableting costs for orally disintegrating tablets are borne by the consumers and patients, and by the finances of the country. Accordingly, the development of technology which enables the tableting of orally disintegrating tablets to be performed easily using inexpensive raw materials has been keenly sought.

In response to such demands, Patent Document 1 proposes an orally disintegrating tablet of the composition described below (see Claim 1).

"An orally disintegrating tablet containing a processed starch having a degree of gelatinization of 30 to 60% dispersed throughout the tablet, and also containing a medication and a saccharide."

During tableting of the orally disintegrating tablet of the composition described above, in order to ensure favorable oral disintegratability, lactose and/or D-mannitol must be added to lower the moldability (see claims 8, 10 and 14, and paragraph 0021 of the same document). At the same time, a water-soluble polymer such as a crystalline cellulose (for example, hydroxypropyl cellulose) must be added to the mixture to impart satisfactory hardness (see claim 11 and paragraph 0024 of the same document).

The orally disintegrating tablet disclosed in this Patent Document 1 uses comparatively inexpensive starch. However, as described above, auxiliary excipients such as a saccharide and a crystalline cellulose must be added separately from the starch. As a result, it cannot necessarily be claimed that the raw material costs are inexpensive and the tableting costs are also inexpensive.

On the other hand, Patent Document 2 discloses a method for producing starch particles having the composition described below.

"A method for producing starch particles, the method including coating the surface of a fluid β-type starch with an α-type starch by spraying a starch paste onto the β-type starch and then performing heating and drying, thereby generating a proportion of the α-type starch on the surface of the β-type starch equivalent to 5 to 20% of the total."

However, these starch particles are not produced with the intention of achieving oral disintegratability for tablets, and in a similar manner to Patent Document 1, require the addition of a saccharide such as lactose or a syrup or the like as an auxiliary excipient (see Patent Document 2, Reference Examples 1 to 4), meaning they suffer from the same problems as described above.

DOCUMENTS OF RELATED ART

Patent Documents

Patent Document 1: International Patent Publication No. 2008/032767 pamphlet
Patent Document 2: Japanese Examined Patent Application, Second Publication No. Sho 58-27774

SUMMARY OF THE INVENTION

Problems to be Solved by the Invention

In light of the above circumstances, an object (aim) of the present invention is to provide a method for producing starch granules which, when used as an excipient during the tableting of an orally disintegrating tablet, can single-handedly impart the tablet with satisfactory oral disintegratability and hardness.

Means to Solve the Problems

As a result of intensive development aimed at addressing the aforementioned problems associated with the conventional technology, the inventors of the present invention discovered that by using the production method described below, the above object could be achieved, and they were thus able to devise the method for producing starch granules described below.

The method includes spraying a starch paste while a β-starch (raw material starch) is being fluidized, thereby bringing the starch paste into contact with each particle of the β-starch and effecting an air-fluidized bed granulation, and subsequently performing fluidized bed drying at a temperature equal to or higher than the gelatinization temperature of the β-starch.

The tablets obtained be performing tableting using the starch granules produced in the manner described above as an excipient have a high degree of hardness, and yet still have favorable oral disintegratability (see Table 2). In other words, tablets having satisfactory oral disintegratability and hardness can be obtained using only the starch granules, without adding auxiliary excipients.

Figure 6:
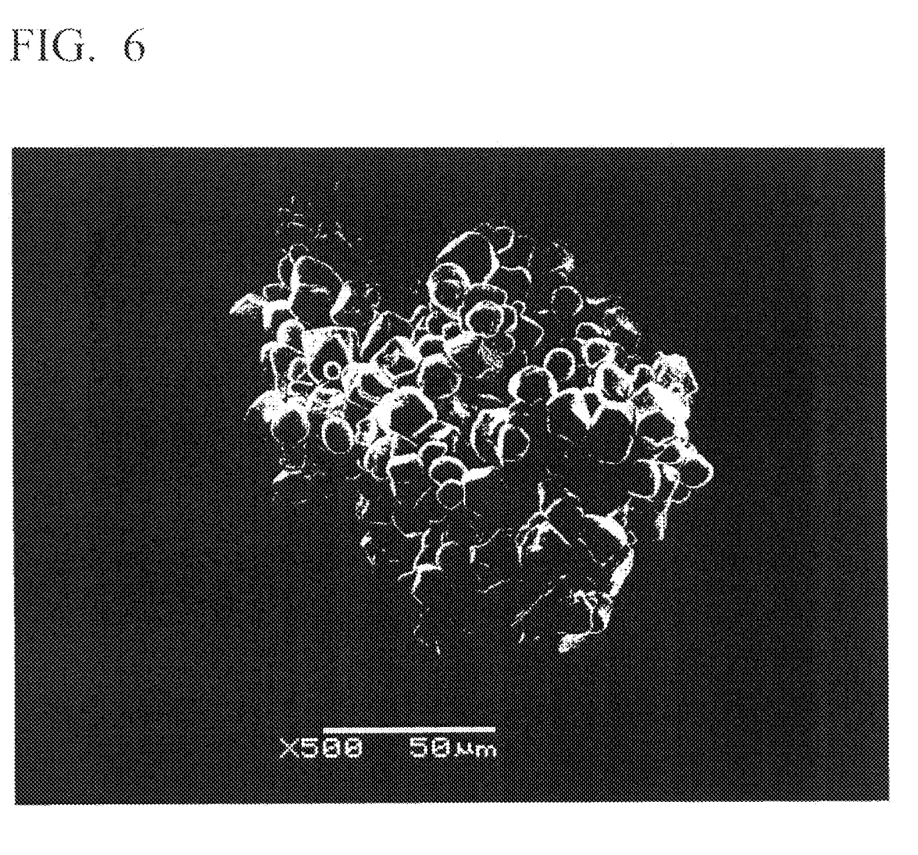
FIG. 6 is an electron microscope photograph (magnification: 500×) illustrating an image of an entire granule from an example of the present invention.

As illustrated in FIG. 6, the starch granules produced by the production method of the present invention are particle conjugates in which a multitude of particles of the β-starch are partially bonded together, with the shape of each particle retained, using the α-starch as a binder. In other words, the α-starch acts as a binder that contributes efficiently to the bonding between particles of the β-starch.

As a result, it is thought that the desired granular strength is achieved with a minimal proportion of the α-starch. Accordingly, tablets that have been tableted (molded) using the granules of the present invention have a prescribed degree of hardness until making contact with saliva inside the mouth. Then, upon contact with saliva inside the mouth, because the proportion of α-starch is small, dissolution occurs rapidly, leading to oral disintegration. Further, as described below, although the degree of compressibility is high, the fluidity is favorable (see Examples 1 and 2, and Reference Examples 1 and 2 in Table 2). Consequently, the starch granules (particle conjugates) of the present invention exhibit favorable moldability (tableting properties), and also contribute to an improvement in the tablet hardness.

A corresponding Example 2 in Patent Document 2 differs from the method of the present invention in terms of the fluidized bed system, the spraying rate, and the total spray amount, as described below.

In this corresponding Example 2, an agitated fluidized bed was used, the spraying rate was a high value of 1,000 parts/minute (100 L/minute) per 100 parts (10 kg) of the β-starch, and the total spray amount was 5,000 parts (500 L). Accordingly, it is assumed that the granular form in Patent Document 2 would contain slightly enlarged particles in which individual particles of the β-starch were coated with the α-starch, and therefore differs from the form illustrated in FIG. 6 of the present invention (see FIG. 1 to FIG. 4 of Patent Document 2).

EMBODIMENTS FOR CARRYING OUT THE INVENTION

The method for producing starch granules according to the present invention is described below in detail.

Special technical terms used in the present description and the claims, other than the technical terms described above, are defined below.

"Orally disintegrating tablet", "Oral disintegratability":

An orally disintegrating tablet means a tablet which, when taken without ingesting any water, disintegrates inside the mouth under essentially only the action of saliva within a period of 40 seconds, and preferably within a period of 30 seconds. The oral disintegratability is judged by the above time required for oral disintegration. This oral disintegration time refers to the value obtained when the tablet is placed in the mouth and the tongue and the like are moved naturally. For example, the oral disintegration time can be determined by placing a tablet for measurement inside the mouth of a healthy adult male without including any moisture inside the mouth, and then measuring the time required for the tablet to disintegrate completely under only the action of saliva. During this measurement, there is no need to restrict natural movement of the tongue and the like (cited from paragraph 0012 of Patent Document 1).

"Degree of Gelatinization"

The method used for measuring the degree of gelatinization (degree of alphatization) employed the common glucoamylase method ("Handbook of Starch Science", edited by Ziro Nikuni, Asakura Publishing Co., Ltd., 1977, page 242). Specifically, the degree of gelatinization was measured in accordance with the method described below.

First, 1 g of glucoamylase was dissolved in 100 mL of water, and the resulting supernatant liquid was used as an enzyme liquid.

Next, 8 mL of water was added to a 100 mg sample (equivalent dry mass) to prepare a suspension. A 2 mL sample of the suspension was injected into each of two test tubes to prepare a sample test liquid and a completely gelatinized test liquid. To the sample test liquid were added 1.6 mL of a 2 mol/L acetic acid buffer (pH 4.8), 0.4 mL of water, and 1 mL of the enzyme liquid. To the completely gelatinized test liquid were added 0.2 mL of 10 N NaOH, 1.6 mL of 2 mol/L acetic acid, 0.2 mL of water, and 1 mL of the enzyme liquid. These test liquids were reacted at 37° C. for 60 minutes. Subsequently, 10 mL of 25 mmol/L of HCl was added to a 0.5 mL sample of each of the reaction liquids to halt the reactions. For each liquid, a 0.5 mL sample of the supernatant liquid was extracted, and 0.5 mL of water and 1.0 mL of the Somogyi reagent were added. Each liquid was then heated for 10 minutes in boiling water, and subsequently cooled. Next, 1 mL of the Nelson reagent was added, and after 3 minutes, the volume of the sample was made up to a total volume of 10 mL with pure water. The absorbance at a wavelength of 660 nm was then measured. The degree of gelatinization was determined using the following formula.

$$\text{Degree of gelatinization} = [(Aa - A_0)/(Ab - A_0)] \times 100$$

[In the formula, a represents the absorbance of the sample test liquid, Ab represents the absorbance of the completely gelatinized test liquid, and $A_0$ represents the absorbance of a blank] (cited from paragraph 0013 of Patent Document 1).

"Particle Size"

A range determined by sieve classification. In other words, a plurality of sieves with different mesh sizes are stacked in order of mesh size, with the largest sieve positioned at the top, the powder to be measured is introduced onto the uppermost sieve, and classification is then performed by oscillating the sieves, either by hand or mechanically, with the mesh size above an arbitrary sieve being recorded as the lower limit and the mesh size below the sieve being recorded as the upper limit.

"Starch Paste Concentration"

The percentage concentration (wt %) of the mass of the β-starch (assuming a water content of 12.5%) relative to the mass of water used in preparation of the starch paste.

"Tablet Hardness"

This means the hardness of a tablet that has been molded by a tableting process. The tablet hardness is represented by the force required (units: N) to crush the tablet, and a larger numerical value indicates a larger breaking strength. In the present invention, the hardness was measured using a "Portable Checker PC-30" (a load cell tablet hardness meter, manufactured by Okada Seiko Co., Ltd.).

"Degree of Compressibility"

Calculated using the following formula.

Degree of compressibility=100×(compacted bulk density−loose bulk density)/compacted bulk density The bulk density values were measured using a "Powder Tester PTX" (manufactured by Hosokawa Micron Group).

The special feature of the method for producing starch granules according to the present invention can be basically described as using an air-fluidized bed to spray a starch paste while a β-starch (raw material starch) is being fluidized, thereby bringing the starch paste into contact with each particle of the β-starch and effecting a fluidized bed granulation in which the dispersed substance (α-starch) within the starch paste is adhered to the particles of the β-starch, and subsequently performing fluidized bed drying at a temperature equal to or higher than the gelatinization temperature.

In the above description, there are no particular limitations on the types of raw material starches used in the β-starch (raw starch) and the starch paste, but the starches are preferably selected from the group consisting of cornstarch, wheat starch, potato starch, rice starch and tapioca starch. These starches are preferred because they are highly versatile and readily available.

In the above description, the air temperature of the air-fluidized bed is typically from 60 to 90° C., and is preferably set within a range from 65 to 80° C. If the air temperature is too high, then there is a possibility that deterioration of the β-starch may occur, which is undesirable.

The average particle size (median size) of the β-starch may be selected appropriately within a range from 1 to 100 μm, and preferably within a range from 5 to 50 μm.

The method used for preparing the starch paste may be a conventional method. For example, the starch paste may be prepared by dispersing and mixing about 3% of a β-starch (raw starch) in room temperature water (not necessarily pure water), and then heating at a temperature of at least 60° C.

The starch concentration of the starch paste during this preparation is typically from 1 to 6%, preferably from 1 to 3.5%, and more preferably from 2.5 to 3.5%. If the starch concentration is too high, then spraying becomes difficult, whereas if the starch concentration is too low, the time required to obtain granules of the desired size becomes too long, and the drying time also lengthens, causing a deterioration in productivity.

The spraying rate for the starch paste when the paste concentration is from 1 to 6% is typically set at 0.2 to 5 parts/minute, and preferably 0.5 to 3 parts/minute of the starch paste per 100 parts of the β-starch. As the granulation proceeds, the swirl of fine powder gradually reduces. The total spray amount of the starch paste, in the case of the same paste concentration of 1 to 6% described above, varies depending on the spraying and fluidization conditions, but is typically from 30 to 70 parts, and preferably from 50 to 65 parts, per 100 parts of the β-starch.

If the starch paste solidifies as a result of a decrease in temperature or the like, then trouble may occur within the solution supply path or the state of the spray. As a result, the starch paste is typically maintained at an appropriate temperature of at least 60° C., and preferably at a temperature within a range from 60 to 90° C., and more preferably from 75 to 85° C.

By spraying the starch dispersion onto the β-starch in this manner, fluidized bed granulation occurs with the particles of the β-starch acting as nuclei and the α-starch within the paste functioning as a binder.

Subsequently, fluidized bed drying is performed while fluidization is continued. The drying temperature at this time (the air temperature of the fluidized bed) is set to a temperature equal to or higher than the gelatinization temperature of the β-starch, which may vary depending on the type of β-starch (raw material starch), but is typically within a range from 80 to 110° C., and preferably from 90 to 110° C. However, in order to accelerate the gelatinization of the granules and improve the drying efficiency, the drying temperature is typically set to a temperature 10 to 20° C. higher than the air temperature of the air-fluidized bed.

If the above drying temperature is too high, then as described below, the degree of gelatinization increases, leading to a higher degree of hardness for the tablets, but ensuring favorable oral disintegratability for the tablets tends to become difficult.

The water content (based on the dried mass) of the dried granulated starch is about 6 to 12%, and preferably about 8 to 11% (see Table 2).

The granular starch of Example 1 produced in this manner has a degree of compressibility of 20 to 30%. Typically, a degree of compressibility of 20 to 30% results in poor fluidity (with a lower degree of compressibility yielding better fluidity). However, as shown in Table 2, compared with the gelatinized cornstarch of Control Example 2 which has a similar degree of compressibility, the angle of repose is nearly 5° smaller, meaning satisfactory fluidity can be ensured. Starch granules produced by the agitation granulation method of Comparative Example 1 also have a similarly low angle of repose, indicating that the fluidity can generally be increased by granulation. However, as illustrated by Comparative Example 1, when granules that have been produced by an agitation granulation method are converted to tablets, they exhibit clearly different properties, and obtaining orally disintegrating tablets with an appropriate degree of hardness is difficult.

As described below, when starch granules that have been molded in this manner are tableted, a good balance between the oral disintegratability and the hardness can be achieved, even with essentially no addition of either one or both of other oral disintegratability imparting agents and hardness imparting agents.

The degree of gelatinization of the starch granules may be set appropriately, in accordance with the required properties, within a range from 1 to 15%, and preferably from 3 to 12%. If the degree of gelatinization is high, then because the proportion of α-starch that functions as a binder is high, tablets with a high degree of hardness can be obtained with ease, but the oral disintegratability tends to deteriorate. In contrast, if the degree of gelatinization is low, then because the proportion of α-starch that functions as a binder is low, the oral disintegratability improves, but obtaining tablets with a high degree of hardness becomes more difficult. When it is desirable to obtain tablets having a high degree of hardness, the degree of gelatinization is set to a higher value.

Figure 1:
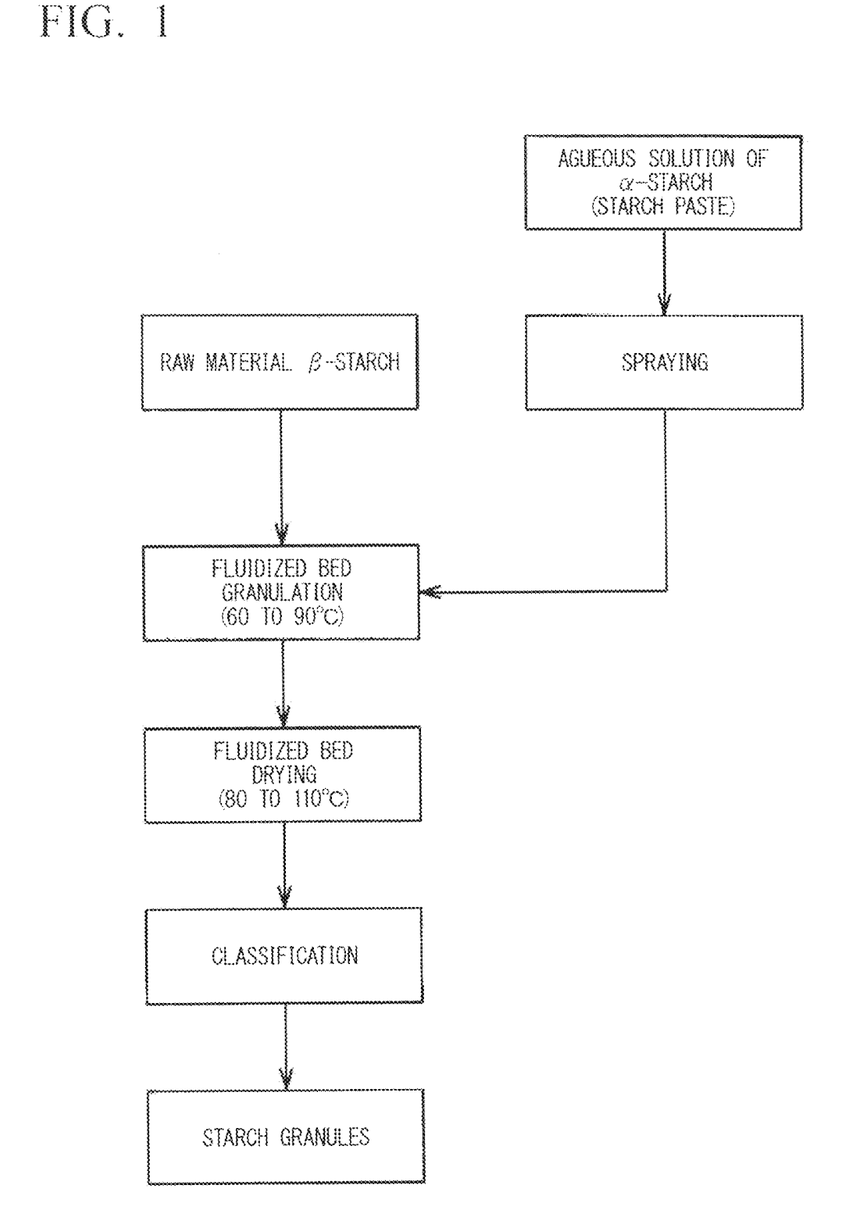
FIG. 1 is a process diagram illustrating the method for producing starch granules of the present invention.
Figure 2:
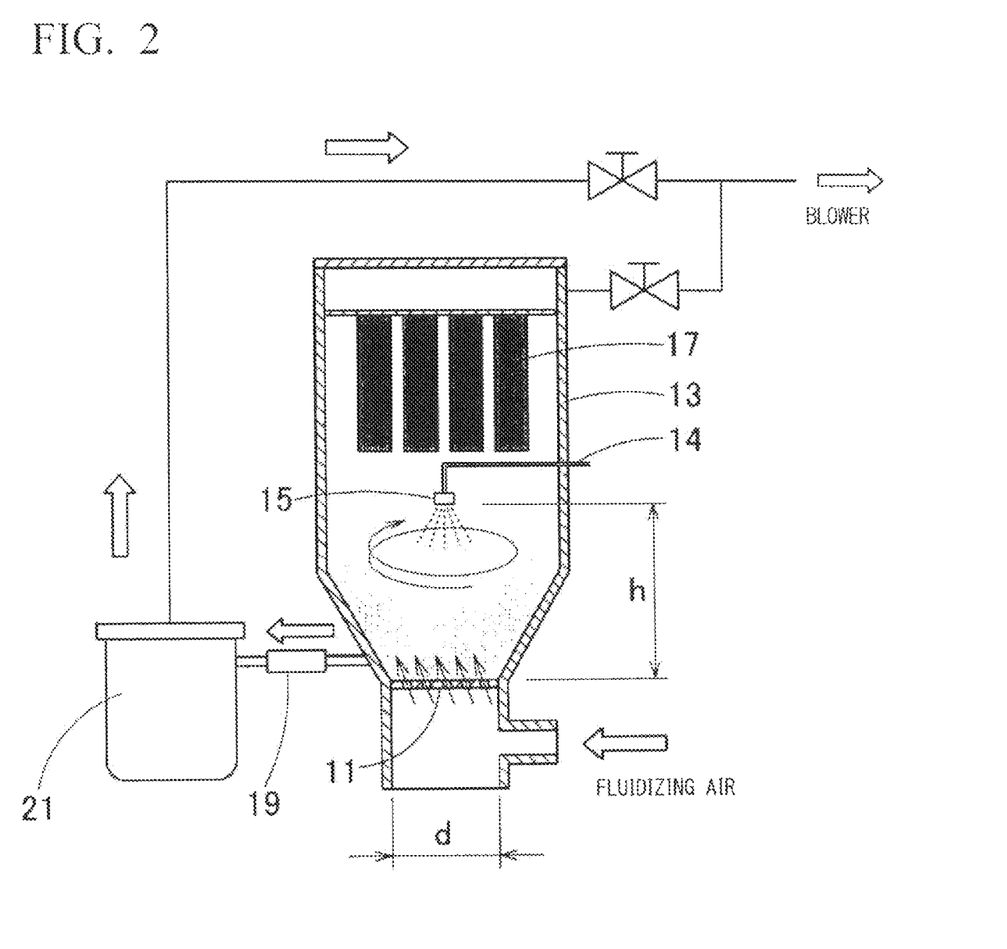
FIG. 2 is a schematic illustration of a fluidized bed granulator used for the granulation performed in each of the examples.

A specific example of a device that can be used favorably as the fluidized bed granulation and drying device that provides the air-fluidized bed is illustrated in FIG. 2.

The device includes a stationary dispersion plate (directional screen) 11, and a fluidization air flow is fed into the device from below, generating a swirling air flow that forms the fluidized bed of the introduced particles. The fluidized bed container 13 is provided with a spray nozzle 15, which is positioned facing the dispersion plate 11 and is connected to a paste line 14, and is also provided with a bag filter 17 in the upper portion of the container. By switching a switching valve 19, the swirling air flow enables the dried product (starch granules) to be collected in a collection tank 21.

In the structure described above, other fluidized bed granulation and drying devices which do not employ the swirling flow system (such as the "WSG series", a product name manufactured by Powrex Corporation) can also be used for the fluidized bed granulation and drying of the present invention.

The starch granules produced in this manner can be produced, with the exception of foreign matter, entirely from the tablet raw materials. However, in those cases where the variation in particle size is large, the smallest and largest particles may be removed by classification in order to enable the desired levels of oral disintegratability and hardness to be obtained in a more stable manner. In other words, it is thought that because the particles of small particle size tend to be more likely to have a proportion of α-starch that is too low, and the particles of large particle size tend to be more likely to have a proportion of α-starch that is too high, these particles have an effect on the variation in the oral disintegratability.

The starch granules that have undergone fluidized bed granulation in the manner described above are mixed with a medicinal component and then tableted. There are no particular limitations on the tableting method, and compression molding methods (briquetting roller, tableting) and extrusion molding methods (screw, rotary perforated die) and the like can be used favorably. Because the medicinal component is added in a small proportion relative to the starch granules, it is thought to have little effect on the evaluations of tablets formed solely from the starch granules, and thus evaluations were performed using tablets containing only the starch granules.

During tableting, the starch granules produced using the method of the present invention can be used to obtain tablets with excellent oral disintegratability and satisfactory hardness (breaking strength) by a direct compression method, even without the addition of additives such as other oral disintegratability imparting agents or hardness imparting agents.

The tablets molded in the present invention have an oral disintegration time of not more than 40 seconds, and preferably not more than 30 seconds, and have a hardness of at least 55 N, and preferably 70 N or greater.

Furthermore, by performing granulation, the angle of repose tends to decrease, and the fluidity improves. As a result, the productivity during tableting can be improved, which contributes to a reduction in tableting costs.

EXAMPLES

Descriptions of Examples 1 and 2, which were conducted together with comparative examples and control examples to confirm the effects of the present invention, are presented below. However, the present invention is in no way limited by these examples.

Example 1

The fluidized bed granulation and drying device used an air-fluidized bed granulator of the structure illustrated in FIG. 2, having specifications including an input capacity of 12 L, a fluid dispersion plate diameter d of 230 mm, and a nozzle height h of 600 mm.

Further, the starch paste was prepared in the manner described below, and was held at a temperature of 60° C. or higher.

A cornstarch (β-starch) produced by Nihon Cornstarch Corporation and having the properties shown in the column for Control Example 1 in Table 2 (hereafter referred to as simply "cornstarch") was used. The starch paste was prepared by adding the cornstarch (β-starch) to room temperature pure water, heating to 90° C., and stirring until a visually transparent mixture was obtained (a uniform phase was formed).

Five kg of the cornstarch was placed in the fluidized bed container 13, and 80° C. air was blown into the container from below the dispersion plate 11 at each of the prescribed flow rates shown below for each of the times shown below, thereby generating a swirling air flow above the dispersion plate 11, and maintaining a fluidized bed of the introduced starch for a period of 40 minutes.

0 to 4 min: 1.2 m$^3$/min, 5 to 9 min: 1.4 m$^3$/min, 10 to 40 min: 1.5 m$^3$/min.

At the same time, the 3% starch paste described above was sprayed into the container at 83 g/min for the first 4 minutes (0 to 4 min), at 83 g/min for the next 5 minutes (5 to 9 min), and then at 75 g/min for the subsequent 31 min (10 to 40 min) to effect fluidized bed granulation (cohesion).

Subsequently, with formation of the fluidized bed maintained at the same flow rate of 1.5 m$^3$/min, a heated drying treatment was performed under conditions of 100° C.×31 min (41 to 71 min), thus obtaining starch granules of Example 1.

The main conditions are shown in Table 1. The water content of the obtained starch granules was 7.0% (see Table 2). In Table 1, the numerical values shown inside parentheses in the lower line of each cell represent the amounts relative to 100 parts of the raw material (this also applies for Example 2 and Comparative Example 1).

Example 2

Instead of using the swirling air flow fluidized bed granulation and drying device used in Example 1, a WSG-30 device mentioned above (capacity: 100 L) was used, and the process volume was scaled up (by a factor of 5).

A starch paste having a concentration of 3% was prepared in the same manner as Example 1.

Twenty five kg of the cornstarch was placed in the fluidized bed container, and 85° C. air was blown into the container from below the dispersion plate at a flow rate of 10 m³/min, thereby maintaining a fluidized bed of the introduced starch for a period of 50 minutes.

At the same time, the 3% starch paste was sprayed into the container with the spraying rate adjusted within a range from 300 to 500 g/min, thus performing fluidized bed granulation (cohesion).

Subsequently, with formation of the fluidized bed maintained at the same flow rate of 10 m³/min, a heated drying treatment was performed under conditions of 100° C.×20 min, thus obtaining starch granules of Example 2.

The main conditions are shown in Table 1. The water content of the obtained starch granules was 8.4% (see Table 2).

Comparative Example 1

Figure 3:
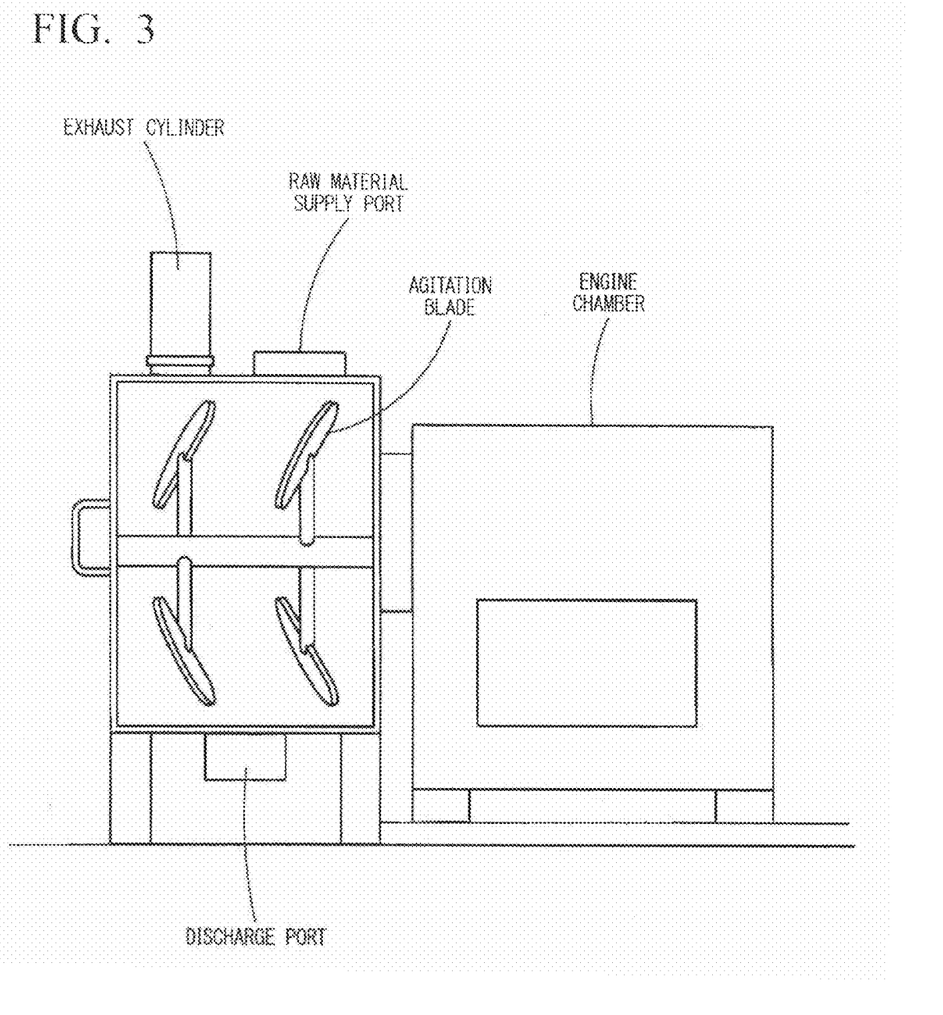
FIG. 3 is a schematic illustration of an agitation granulator used for the granulation in Comparative Example 1.
Figure 4:
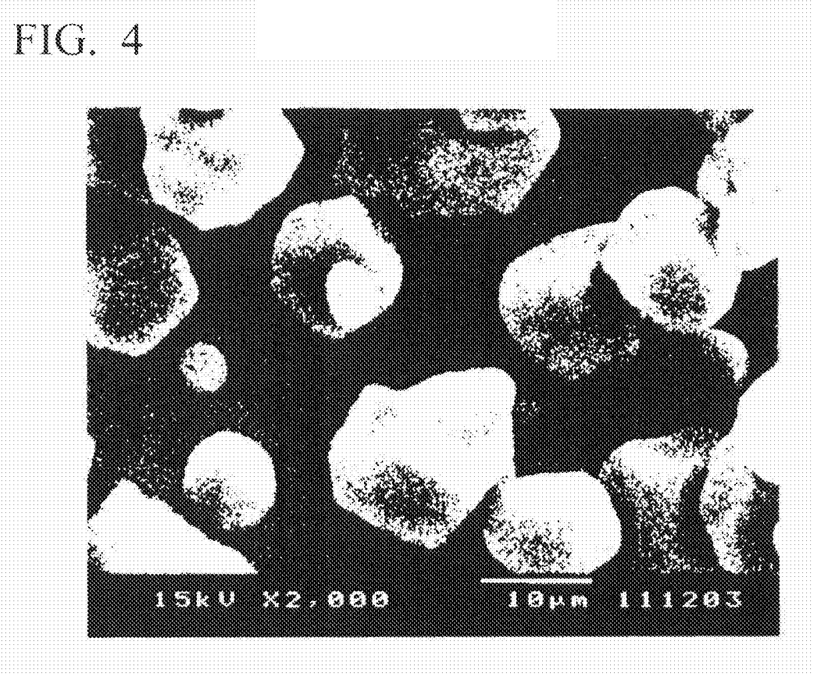
FIG. 4 is an electron microscope photograph (magnification: 2,000×) of typical cornstarch.
Figure 5:
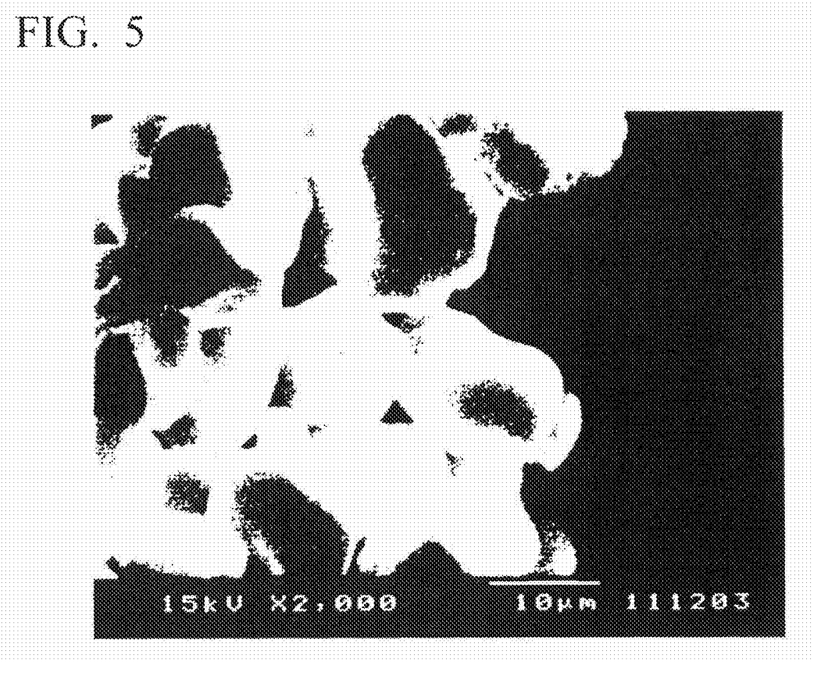
FIG. 5 is an electron microscope photograph (magnification: 2,000×) of the surface of a granule from an example of the present invention.

Using a similar procedure to Example 1, but using the agitation granulator illustrated in FIG. 3, a 3% starch paste-like starch dispersion was dripped into the granulator under the conditions shown in Table 1, at a rate sufficient to achieve the supply rate shown in the table, and an agitation granulation was performed. The granulated product was subjected to vibrating fluidized bed drying using a vibrating fluidized bed dryer (VUA-20, manufactured by Chuo Kakohki Co., Ltd.) under conditions of 90° C.×30 minutes, thus obtaining a granulated starch of Comparative Example 1.

In a similar manner to Example 1, the main conditions are shown in Table 1. Further, the water content of the obtained starch granules was 5.6% (see Table 2).

The starch granules of Example 1 and Comparative Example 1 were subjected to sieve classification by collecting the particles that did not pass through a mesh of 100 μm but passed through a mesh of 180 μm (100 to 180 μm), and these collected particles were used as tablet raw materials.

The properties of each type of starch granules prepared in this manner are shown in Table 2. It is evident that the granules of Example 1 had a higher degree of gelatinization and a slightly lower angle of repose, and exhibited favorable fluidity. It is clear that the angle of repose was at least 10° lower than that of cornstarch. In other words, as illustrated in Example 1 and 2, it was confirmed that in the present invention, for a degree of compressibility within a range from 20 to 30%, granules with an angle of repose (fixed funnel method) of 30 to 40° were able to be obtained. In particular, in Example 1, although the degree of compressibility is higher than that of α-starch, it is evident that the angle of repose is clearly lower than that of α-starch, resulting in superior fluidity. The angle of repose is also slightly lower than that of Comparative Example 1 which exhibits a similar degree of compressibility.

Using the starch granules of these Examples 1 and 2 and Comparative Example 1, cornstarch (Control Example 1), an α-cornstarch manufactured by Nihon Cornstarch Corporation (Control Example 2), together with a commercial product A (Reference Example 1) and a commercial product B (Reference Example 2) marketed as starch granules for tableting, a 200 mg sample of each substance was tableted by compression molding (under conditions including a compression rate of 10 mm/min and a compressive force of 1000 kgf), and each of the thus obtained tablets (diameter 8 mm×thickness 3 mm) was measured for hardness and oral disintegratability.

The properties of each of the tablets are shown in Table 2. The commercial product A is a tableting granule produced by spray granulation of cornstarch. The commercial product B is a starch granule for tableting produced by granulating a high amylose cornstarch.

The tablets obtained by performing compression molding of the granules of the present invention from Example 1 exhibited the targeted hardness of at least 55 N, and easily satisfied the condition for favorable oral disintegratability of an oral disintegration time of not more than 30 seconds, despite containing no added auxiliary excipients such as a saccharide. Useful starch granules were obtained that exhibited a good balance between the two opposing properties observed for tablets. Even though the degree of gelatinization of the granules was relatively low, it was confirmed that tablets having a high degree of hardness (high strength) were able to be obtained.

However, when the β-starch of Control Example 1 was used as the raw material, although the targeted level of oral disintegratability was able to be achieved, obtaining the required degree of hardness was difficult, whereas when the α-starch of Control Example 2 was used as the raw material, not only was it difficult to obtain the required hardness, but the tablets also lacked the desired oral disintegratability.

Moreover, when the commercial product A of Reference Example 1 was used as the raw material, although the targeted degree of hardness was obtained, obtaining satisfactory oral disintegratability proved difficult, whereas when the commercial product B of Reference Example 2 was used as the raw material, although a hardness considerably higher than the targeted value was obtained, the oral disintegratability was poor.

TABLE 1

|  | Example 1 | Example 2 | Comparative Example 1 |
|---|---|---|---|
| Amount added of raw material β-starch | 5 kg (100 parts) | 25 kg (100 parts) | 5 kg (100 parts) |
| Concentration of starch paste (α-starch) | about 3% | about 3% | about 3% |
| Starch paste spraying (supply) time | 38 min | 50 min | 3.5 min |
| Starch paste spraying (supply) rate | 75 to 83 g/min (1.5 to 1.66 parts/min) | 200 to 500 g/min (0.8 to 2.0 parts/min) | 610 g/min (12.2 parts/min) |
| Starch paste spraying (supply) amount | 2.92 kg (58.4 parts) | 15.0 kg (60 parts) | 1.83 kg (36.6 parts) |
| Amount added of α-starch | 87.6 g (1.75 parts) | 450 g (1.8 parts) | 54.9 g (1.10 parts) |
| α((β + α) | 0.0172 | 0.0177 | 0.010 |
| Drying conditions after granulation | 100° C. × 31 min | 100° C. × 20 min | 90° C. × 30 min |

TABLE 1-continued

| | Example 1 | Example 2 | Comparative Example 1 |
|---|---|---|---|
| Degree of gelatinization of starch granules | 5.3% | 6.4% | 4.3% |

TABLE 2

| | | Example 1 Tablet | Example 2 Tablet | Comparative Example 1 Tablet | Control Example 1 Tablet | Control Example 2 Tablet | Reference Example 1 Tablet | Reference Example 2 Tablet |
|---|---|---|---|---|---|---|---|---|
| Granules/powder properties | Raw material name | Example 1 (granules) | Example 2 (granules) | Comparative Example 1 (granules) | Cornstarch | α-Cornstarch | Commercial product A | Commercial product B |
| | Particle size (μm) | 100 to 180 | *150 | 100 to 180 | 5 to 20 | 198 (average) | 150.0 | 116.5 (average) |
| | Water content (%) | 7.0 | 8.4 | 5.6 | 12.6 | 8.4 | 9.1 | 11.0 |
| | Angle of repose (°) | 34.7 | 34.6 | 35.8 | 48.4 | 39.1 | 35.0 | 37.0 |
| | Degree of gelatinization (%) | 5.3 | 6.4 | 4.3 | 3.6 | 96.7 | 7.8 | — |
| | Loose bulk density (g/cm$^3$) | 0.38 | 0.36 | 0.43 | 0.37 | 0.37 | 0.56 | 0.45 |
| | Compacted bulk density (g/cm$^3$) | 0.53 | 0.46 | 0.60 | 0.66 | 0.50 | 0.61 | 0.49 |
| | Degree of compressibility | 28.30 | 21.90 | 28.33 | 43.94 | 26.00 | 10.7 | 8.17 |
| Tablet properties | Hardness (N) | 88.7 | 83.0 | 18.5 | 40.0 | 238.7 | 87.0 | 312.0 |
| | Oral disintegratability (s) | 17 | 19 | 18 | 8 | >3600 | 74 | 160 |

*55% residual particle size

Further, as an evaluation of the disintegratability of the present invention, the swelling ratio upon water absorption was measured for various starches including that of Example 1.

The swelling ratio upon water absorption was measured in the manner described below.

At room temperature (15 to 25° C.), a 10 g sample was placed in a measuring cylinder, and the volume of the sample was measured and recorded as the volume before swelling. Water was then added to bring the volume to 100 ml, and the volume of the sample after one hour had elapsed was recorded as the volume after swelling. The value obtained by dividing the volume after swelling by the volume before swelling can be recorded as the swelling ratio upon water absorption. The results of investigating the swelling ratio upon water absorption for a typical cornstarch (Control Example 1), granules of an example of the present invention (Example 1), the commercial product A (Reference Example 1), the commercial product B (Reference Example 2), and the gelatinized cornstarch manufactured by Nihon Cornstarch Corporation (Control Example 2) are shown in Table 3.

Figure 7:
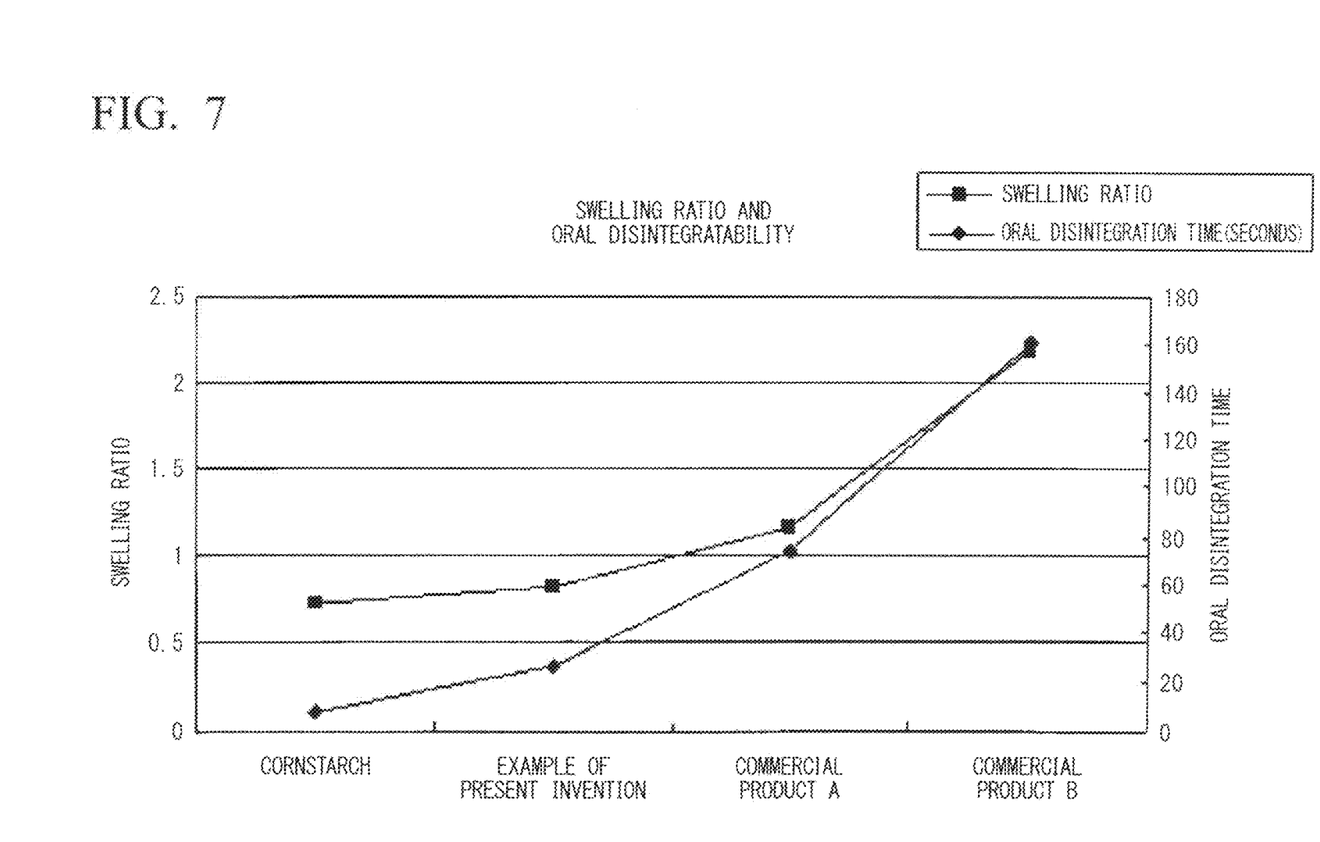
FIG. 7 is a graph illustrating the relationship between the swelling ratio and the oral disintegration time, and indicates the results of tests performed on various starches.

Summarizing the relationship between the swelling ratio and the oral disintegratability based on the results shown in Table 3 yields the type of relationships shown in FIG. 7. The product from Nihon Cornstarch Corporation, and the corn-based additives of the commercial products exhibited different relationships between the swelling ratio and the oral disintegration time. The granules of Example 1, which represents an example of the present invention, exhibited a clearly different swelling ratio from those of the existing commercial granules. Moreover, it is evident that the tablets produced by molding (tableting) the starch granules of the present invention had a significantly shorter oral disintegration time than the tablets molded using the granules of the commercial products (commercial products A and B) (see Table 2).

DESCRIPTION OF THE REFERENCE SIGNS

11: Dispersion plate (directional screen)
13: Fluidized bed container
14: Paste line
15: Spray nozzle

TABLE 3

| | Control Example 1 | Control Example 2 | Example of present invention | Reference Example 1 | Reference Example 2 |
|---|---|---|---|---|---|
| Sample | Cornstarch | α-Cornstarch | Example 1 (granules) | Commercial product A (granules) | Commercial product B (granules) |
| Before swelling (mL) | 22 | 23 | 29 | 19 | 21 |
| After swelling (mL) | 16 | 88 | 22 | 22 | 46 |
| Swelling ratio (%) | 0.73 | 3.83 | 0.82 | 1.16 | 2.19 |

17: Bag filter
19: Switching valve
21: Collection tank

The invention claimed is:

1. Starch granules, comprising:
   100 parts of particles of β-starch; and
   a binder comprised of α-starch present in an amount to include from 0.3 to 4.2 parts of said α-starch within the starch granules, wherein
   the starch granules are present in the form of particles of β-starch partially bonded together with the binder comprised of α-starch,
   wherein a degree of gelatinization of the starch granules is from 1 to 15%, and
   wherein, at a degree of compressibility of 20 to 30%, the starch granules exhibit an angle of repose (fixed funnel method) of 30 to 40°.

2. The starch granules according to claim 1, wherein a water content thereof is from about 6 to 12%.

3. The starch granules according to claim 1, wherein a water content thereof is from about 8 to 11%.

4. The starch granules according to claim 1, wherein a degree of gelatinization of the starch granules is from 3 to 12%.

5. The starch granules according to claim 1, wherein a degree of gelatinization of the starch granules is from 5.3 to 6.4%.

6. The starch granules according to claim 1, wherein the starch granules are capable of providing a tablet that exhibits an oral disintegration time of not more than 40 seconds and a hardness of at least 55 N, the tablet being formed by compression molding 200 mg of the starch granules to a diameter of 8 mm×a thickness of 3 mm.

7. An orally disintegrating tablet, produced by tableting the starch granules according to claim 1, with essentially no addition of either one or both of other oral disintegratability imparting agents and hardness imparting agents.

8. The orally disintegrating tablet according to claim 7, which exhibits an oral disintegration time of not more than 40 seconds, and a hardness of at least 55 N.

9. The orally disintegrating tablet according to claim 7, which exhibits an oral disintegration time of not more than 40 seconds and a hardness of at least 55 N, the tablet being formed by compression molding 200 mg of the starch granules to a diameter of 8 mm×a thickness of 3 mm.

10. The orally disintegrating tablet according to claim 9, which
    exhibits an oral disintegration time of not more than 19 seconds and a hardness of from 55 N to 88.7 N, the tablets being formed by compression molding 200 mg of the starch granules to a diameter of 8 mm×a thickness of 3 mm.

11. A method for producing starch granules according to claim 1, the method comprising:
    spraying a paste of α-starch while a β-starch, which is a raw material starch, is being fluidized using an air-fluidized bed, thereby bringing the paste of α-starch into contact with each particle of the β-starch and effecting a fluidized bed granulation, and
    subsequently performing fluidized bed drying at a temperature equal to or higher than a gelatinization temperature of the β-starch.

12. The method according to claim 11, wherein
    a concentration of α-starch in the starch paste is from 1 to 6%,
    a dispersed starch supply rate is from 0.2 to 5 parts by mass/minute per 100 parts by mass of the β-starch, and
    the spraying is performed until a total amount of the paste of α-starch is supplied in an amount of from 30 to 70 parts by mass per 100 parts by mass of the β-starch.

13. The method according to claim 12, wherein
    the spraying is performed with an air temperature of the air-fluidized bed set within a range of from 60 to 90° C., thereby effecting the fluidized bed granulation of the β-starch particles, and the fluidization is then continued, and
    the fluidized bed drying is performed with an air temperature set within a range of from 80 to 110° C. but 10 to 20° C. higher than the air temperature of the air-fluidized bed during the fluidized bed granulation.

* * * * *